(12) United States Patent
Nakamura

(10) Patent No.: US 9,261,662 B2
(45) Date of Patent: Feb. 16, 2016

(54) PHOTOELECTRIC CONVERSION CONNECTOR, OPTICAL TRANSMISSION MODULE, IMAGING APPARATUS, AND ENDOSCOPE

(71) Applicant: OLYMPUS CORPORATION, Tokyo (JP)

(72) Inventor: Mikio Nakamura, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 371 days.

(21) Appl. No.: 13/788,468

(22) Filed: Mar. 7, 2013

(65) Prior Publication Data

US 2013/0182099 A1 Jul. 18, 2013

Related U.S. Application Data

(63) Continuation of application No. PCT/JP2011/070505, filed on Sep. 8, 2011.

(30) Foreign Application Priority Data

Sep. 30, 2010 (JP) ................................. 2010-222342

(51) Int. Cl.
*G02B 6/43* (2006.01)
*A61B 1/00* (2006.01)
(Continued)

(52) U.S. Cl.
CPC .............. *G02B 6/43* (2013.01); *A61B 1/00013* (2013.01); *A61B 1/00126* (2013.01);
(Continued)

(58) Field of Classification Search
CPC ........... A61B 1/00013; A61B 1/00126; A61B 1/051; G02B 6/3624; G02B 6/4202; G02B 6/4206; G02B 6/424; G02B 6/428; G02B 6/43; H04N 7/18; B65B 19/28; G01B 11/022; G01N 21/88; G01N 21/8806
USPC .......................................................... 348/86
See application file for complete search history.

(56) References Cited

U.S. PATENT DOCUMENTS 4,953,539 A * 9/1990 Nakamura et al. ............ 600/109
5,010,876 A * 4/1991 Henley et al. ................. 600/112
(Continued)

FOREIGN PATENT DOCUMENTS

EP 1 482 339 A1 12/2004
JP S63-088873 A 4/1988
(Continued)

OTHER PUBLICATIONS

Extended Supplementary European Search Report dated Nov. 24, 2014 from related European Application No. 11 82 8748.1.
(Continued)

*Primary Examiner* — Shan Elahi
(74) *Attorney, Agent, or Firm* — Scully, Scott, Murphy & Presser, PC

(57) ABSTRACT

A photoelectric conversion connector, includes: an optical element that performs one of inputting and outputting an optical signal; an electric element that controls one of a light emission and a light reception of the optical element; and at least one substrate on which the electric element and the optical element are mounted, the substrate including an aligning and connecting part that allows connecting an optical fiber that performs one of inputting an optical signal output from the optical element and outputting an optical signal input to the optical element, the aligning and connecting part being provided on a surface different from a surface on which the optical element are mounted of the substrate, the optical fiber being connected to the substrate via the aligning and connecting part, and the optical element and the optical fiber being arranged and mounted in line along a direction of a thickness of the substrate.

20 Claims, 10 Drawing Sheets

(51) Int. Cl.
*A61B 1/05* (2006.01)
*G02B 6/42* (2006.01)
*G02B 6/36* (2006.01)

(52) U.S. Cl.
CPC ............ *A61B 1/051* (2013.01); *G02B 6/4202* (2013.01); *G02B 6/4206* (2013.01); *G02B 6/428* (2013.01); *G02B 6/3624* (2013.01); *G02B 6/424* (2013.01)

(56) References Cited

U.S. PATENT DOCUMENTS

| | | | |
|---|---|---|---|
| 5,029,016 A * | 7/1991 | Hiyama et al. | 358/403 |
| 5,432,543 A * | 7/1995 | Hasegawa et al. | 348/45 |
| 5,608,451 A * | 3/1997 | Konno et al. | 348/69 |
| 6,887,111 B2 * | 5/2005 | Nakai et al. | 439/669 |
| 7,513,697 B2 * | 4/2009 | Harano et al. | 385/88 |
| 7,959,642 B2 * | 6/2011 | Nobis et al. | 606/170 |
| 8,956,279 B2 * | 2/2015 | Kitano | 600/110 |
| 2001/0022370 A1 * | 9/2001 | Meyer-Guldner | 257/225 |
| 2002/0118924 A1 * | 8/2002 | Murata | 385/52 |
| 2003/0119369 A1 * | 6/2003 | Nakai et al. | 439/669 |
| 2004/0166928 A1 * | 8/2004 | Kumagai | 463/20 |
| 2005/0226569 A1 | 10/2005 | Sashinaka et al. | |
| 2005/0272975 A1 * | 12/2005 | McWeeney et al. | 600/113 |
| 2006/0128184 A1 * | 6/2006 | Forman | 439/83 |
| 2007/0197865 A1 * | 8/2007 | Miyake et al. | 600/109 |
| 2007/0211426 A1 * | 9/2007 | Clayton et al. | 361/689 |
| 2007/0232860 A1 * | 10/2007 | Kubo et al. | 600/160 |
| 2007/0249186 A1 * | 10/2007 | Ju | 439/71 |
| 2008/0260334 A1 * | 10/2008 | Sakaji et al. | 385/76 |
| 2009/0290836 A1 | 11/2009 | Lee et al. | |
| 2011/0245607 A1 * | 10/2011 | Hayashi et al. | 600/109 |

FOREIGN PATENT DOCUMENTS

| | | |
|---|---|---|
| JP | H03-50355 U | 5/1991 |
| JP | H09-090175 A | 4/1997 |
| JP | 2001-201672 A | 7/2001 |
| JP | 2002-250846 A | 9/2002 |
| JP | 2002-329891 A | 11/2002 |
| JP | 2005-116400 A | 4/2005 |
| JP | 2007-260066 A | 10/2007 |

OTHER PUBLICATIONS

Partial English Language Translation for the relevant part of JP S63-088873 A (Reference was previously cited in an IDS filed Mar. 7, 2013).

Partial English Language Translation for the relevant part of JP 03-050355 U (Reference was previously cited in an IDS filed Mar. 7, 2013).

International Search Report dated Nov. 15, 2011 issued in PCT/JP2011/070505.

* cited by examiner

PHOTOELECTRIC CONVERSION CONNECTOR, OPTICAL TRANSMISSION MODULE, IMAGING APPARATUS, AND ENDOSCOPE

CROSS-REFERENCE TO RELATED APPLICATION

This application is a continuation of International Application No. PCT/JP2011/070505 designating the United States and filed on Sep. 8, 2011 which claims the benefit of priority of the prior Japanese Patent Application No. 2010-222342, filed on Sep. 30, 2010, and the entire contents of the International application and the Japanese Application are incorporated herein by reference.

BACKGROUND OF THE INVENTION

1. Field of the Invention

The present invention relates to a photoelectric conversion connector, an optical transmission module, an imaging apparatus provided with the optical transmission module, and an endoscope.

2. Description of the Related Art

Conventionally, endoscopes for medical and industrial purposes have been widely used, and especially a medical endoscope enables an observation of a diseased site when an insertion part thereof is deeply inserted into an inside of a body and further enables an examination and a treatment of the inside of the body when a treatment tool is used in combination when needed. As such an endoscope, an endoscope provided with an imaging apparatus that includes therein an imaging element such as a CCD at a distal end of an insertion part is available. In recent years, an imaging element having a large number of pixels enabling an observation with clearer images has been developed and an application of such an imaging element having a large number of pixels to an endoscope has been studied. In a case of using an imaging element having a large number of pixels in an endoscope, it becomes necessary to embed an optical transmission module in the endoscope for transmitting signals at high speed between the imaging element and a signal processing device. To reduce a burden on a patient and secure a field of view for observation, it is necessary to reduce a width and a length of a photoelectric conversion connector which is a hard part constituting the optical transmission module to be embedded to the inside of the endoscope as much as possible since a smaller outer diameter of a distal end part of an insertion part of the endoscope and a shorter length of the distal end part are aspired to.

Meanwhile, an optical active connector provided with a case that houses an electric connector, an optical element, and a mounting substrate at predetermined positions has been proposed as a technique regarding an optical active connector that performs a conversion between an optical signal and an electric signal. Detailed information of the technique is obtained in Japanese Patent Application Laid-Open No. 2005-116400, for example.

SUMMARY OF THE INVENTION

According to an aspect of the present invention, a photoelectric conversion connector, includes: an optical element that performs one of inputting and outputting an optical signal; an electric element that controls one of a light emission and a light reception of the optical element; and at least one substrate on which the electric element and the optical element are mounted, the substrate including an aligning and connecting part that allows connecting an optical fiber that performs one of inputting an optical signal output from the optical element and outputting an optical signal input to the optical element, the aligning and connecting part being provided on a surface different from a surface on which the optical element are mounted of the substrate, the optical fiber being connected to the substrate via the aligning and connecting part, and the optical element and the optical fiber being arranged and mounted in line along a direction of a thickness of the substrate.

According to another aspect of the present invention, an optical transmission module, includes: an optical element that performs one of inputting and outputting an optical signal; an electric element that controls one of a light emission and a light reception of the optical element; a cable that performs at least one of inputting and outputting an electric signal to the electric element; an optical fiber that performs one of inputting and outputting an optical signal to the optical element; and at least one substrate on which the electric element, the optical element, the cable, and the optical fiber are mounted, the cable and the optical fiber being mounted on a same surface of the substrate and the electric element, and the electric element and the optical element being arranged and mounted on a surface different from the surface on which the cable and the optical fiber are mounted so that the electric element and the cable are arranged in line, and the optical element and the optical fiber are arranged in line along a direction of a thickness of the substrate.

According to still another aspect of the present invention, in an imaging apparatus, an imaging element is connected to the external connection electrode of the photoelectric conversion connector.

According to still another aspect of the present invention, an endoscope includes the imaging apparatus.

The above and other features, advantages, and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
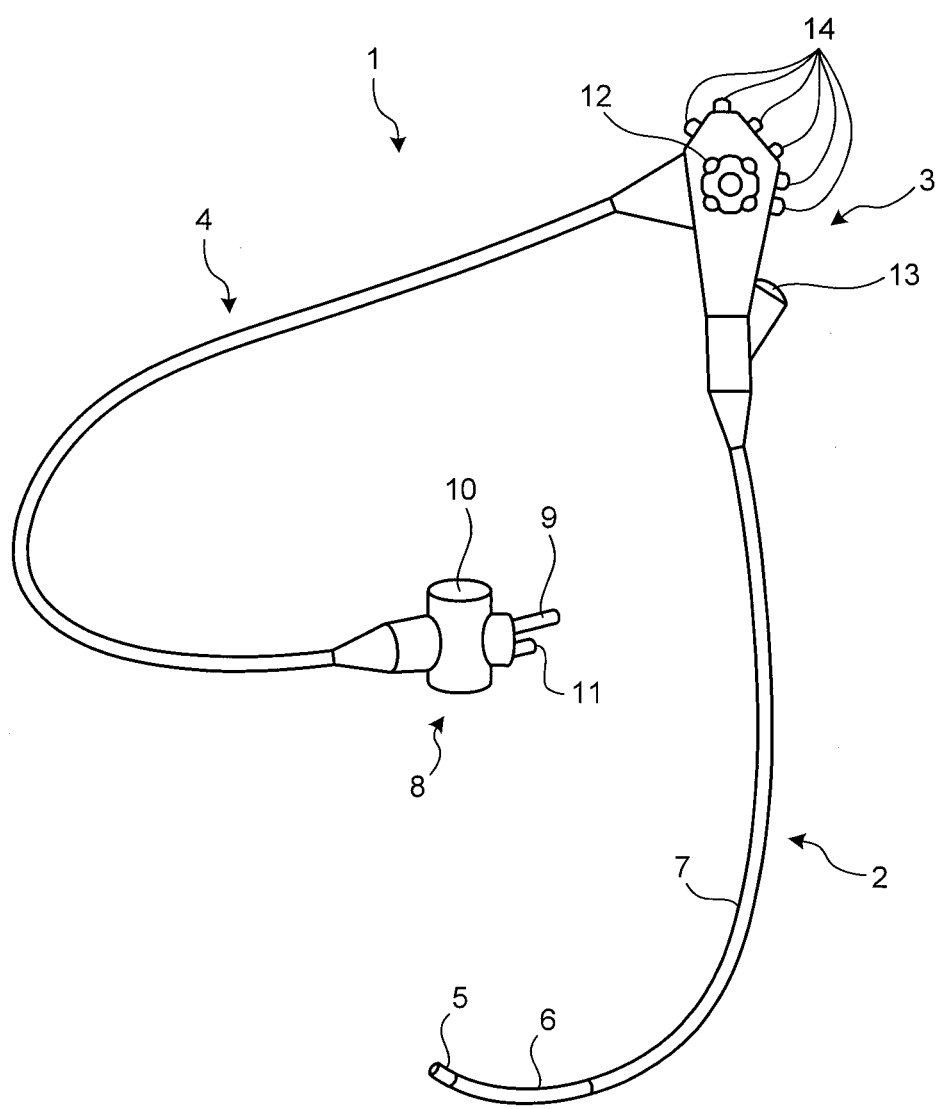
FIG. 1 schematically shows a structure of an endoscope according to the present invention.

Exemplary embodiments of the present invention (hereinafter referred to as "embodiments") will be explained below with reference to the accompanying drawings. It should be noted that the present invention is not limited to the embodiments. Throughout the explanation of the drawings, a common part will be provided with a common reference symbol. It should also be noted that the accompanying drawings are merely schematic and a relation between thickness and width and a ratio among parts may be different from the reality. Besides, there may be parts whose dimensional relations and ratios are mutually different in the drawings.

First Embodiment

An endoscope using an optical transmission module according to a first embodiment will be explained, first. FIG. 1 schematically shows a structure of an endoscope according to the present invention. As shown in FIG. 1, an endoscope 1 using an optical transmission module according to the first embodiment is provided with an elongated insertion part 2, a manipulation part 3 that is provided at a proximal end side of the insertion part 2 and grasped by a manipulator of the endoscope, and a flexible universal cord 4 that extends from a side of the manipulation part 3. The universal cord 4 includes therein a light guiding cable, an electric system cable, an optical fiber, and the like.

The insertion part 2 is provided with a distal end part 5 in which an imaging element such as a CCD is embedded, a bend part 6 that is configured to be bendable by a plurality of bending pieces, and a flexible pipe 7 that has a flexibility and an elongated shape and is provided in a proximal end side of the bend part 6.

A connector 8 is provided at an end part at a side toward which the universal cord 4 extends, and a light guiding connector 9 that is detachably connected to a light source device, an electric contact part 10 that allows transmitting an electric signal of a subject image obtained via a photoelectric conversion in the imaging element to a signal processing device and a control device, an air feeding cap 11 that allows feeding air to a nozzle of the distal end part 5, and the like are provided in the connector 8. Here, the light source device includes therein a light source such as a halogen lamp and supplies a light from the light source to the endoscope 1 connected via the light guiding connector 9 as an illumination light. Besides, the signal processing device and the control device, which supply an electric power to the imaging element and to which the electric signal obtained via the photoelectric conversion from the imaging element is input, process electric signals obtained through the imaging by the imaging element, control a display device to be connected thereto to display an image, and output driving signals for controlling and driving a gain modulation and the like of the imaging element.

In the manipulation part 3, a bend knob 12 that causes the bend part 6 to bend in the vertical direction and the horizontal direction, a treatment tool insertion part 13 through which a treatment tool such as a biopsy forceps and a laser probe is inserted to an inside of a body cavity, a plurality of switches 14 that allow operating a peripheral equipment such as the signal processing device, the control device, and an air/water/gas feeding unit are provided. The endoscope 1 in which a treatment tool is inserted through a treatment tool insertion opening performs a biopsy of harvesting diseased tissues by, for example, the biopsy forceps and the like by projecting a distal end treatment part of the treatment tool by way of a treatment tool insertion channel provided inside.

Figure 2:
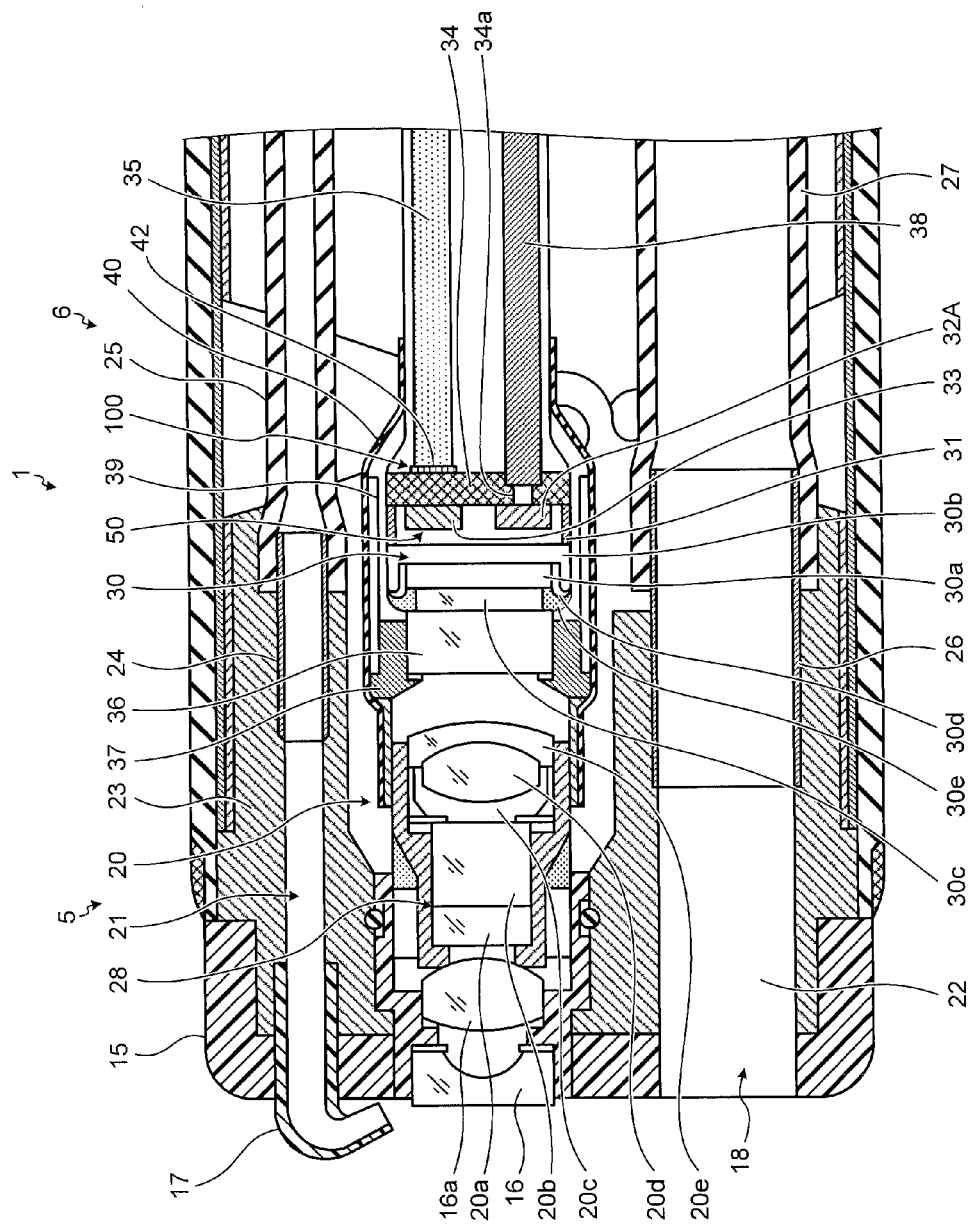
FIG. 2 is a cross sectional view of an inner structure of a distal end part of the endoscope shown in FIG. 1.

Next, a structure of the distal end part of the endoscope will be explained. FIG. 2 is a cross sectional view of an inner structure of the distal end part 5 of the endoscope 1 shown in FIG. 1. As shown in FIG. 2, a distal end part is externally framed by a distal end cover 15 in the distal end part 5 locating at a distal end side of the insertion part 2 of the endoscope 1. In the distal end cover 15, an observation window 16, not shown illumination lens, an air/water feeding nozzle 17, and a forceps opening 18 are provided. In the observation window 16, an imaging apparatus 20 that captures images of an inside of a body cavity via a plurality of lenses including a lens 16a is inserted and fitted. Behind the observation window 16, a distal end block 23 in which an air/water feeding passage 21 and a forceps inserting passage 22 are provided respectively for the nozzle 17 and the forceps opening 18 is arranged.

In a rear end part of the air/water feeding passage 21 in the distal end block 23, an air/water feeding pipe 24, to which an air/water feeding tube 25 is connected, is provided. In a rear end part of the forceps inserting passage 22, a forceps inserting pipe 26, to which a forceps inserting tube 27 is connected, is provided.

The imaging apparatus 20 includes an objective optical unit 28 constituted by a plurality of optical lenses 20a to 20e, an imaging element 30 such as a CCD that is arranged to rearward of the objective optical unit 28 and receives a light having entered the objective optical unit 28, an optical transmission module 100 that transmits image signals in the imaging element 30 to the signal processing device as an external device, and the like.

A cover glass 36 is provided at a light receiving surface side of the imaging element 30, an inner circumferential part of an imaging element retaining frame 37 is fitted in an outer circumferential part of the cover glass 36, and the fitting is integrally fixed by an adhesive agent and the like. In a case of using a CCD unit as an imaging unit, for example, the imaging element 30 includes a CCD chip 30a, a package 30b, a filter 30c, a bonding wire 30d, a sealing resin 30e, and the like.

The optical transmission module 100 is provided with a photoelectric conversion connector 50 that performs a conversion between an optical signal and an electric signal, a cable 35 that supplies a driving signal and a power voltage to the photoelectric conversion connector 50, and an optical fiber 38 that transmits optical signals transmitted from the photoelectric conversion connector 50 to the signal processing device as an external device.

The photoelectric conversion connector 50 is provided with an optical element 32A that converts an image signal as an electric signal transmitted from the imaging element 30 by way of a circuit such as an IC into an optical signal, an electric element 33 that controls a light emission of the optical signal transmitted by the optical element 32A, and a circuit substrate 34 on which the optical element 32A, the electric element 33, and the like are mounted. A spacer 31 is provided between the imaging element 30 and the circuit substrate 34, and a shielding frame 39 is provided at a rear end part of the imaging element retaining frame 37 in a manner of covering the imaging element 30 and the circuit substrate 34. The shielding frame 39 and an outer circumferential part of the imaging element retaining frame 37 at a distal end side are coated by a heat shrinkable tube 40. Here, the imaging element 30 and the optical transmission module 100 are arranged so that a main surface of the imaging element 30 becomes in parallel with the circuit substrate 34 of the optical transmission module 100 via the spacer 31 and the shielding frame 39.

Figure 3:
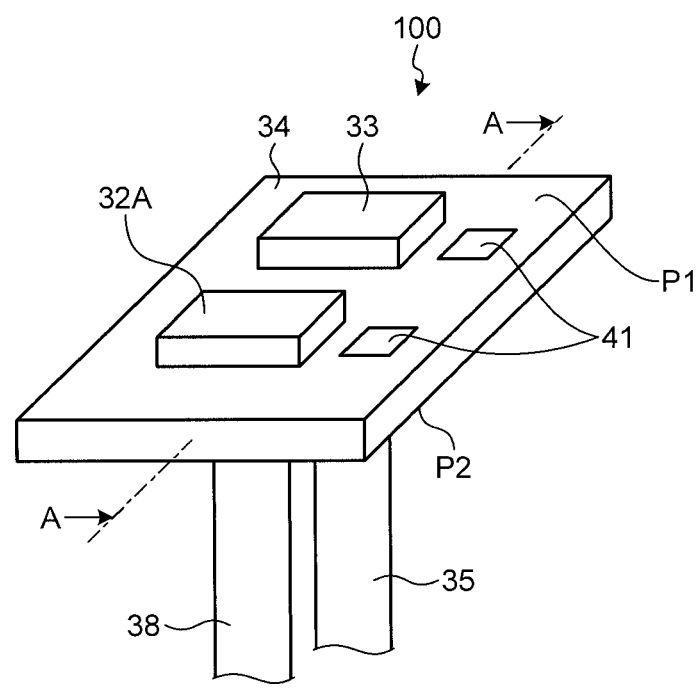
FIG. 3 is a perspective view of an optical transmission module according to a first embodiment.
Figure 4:
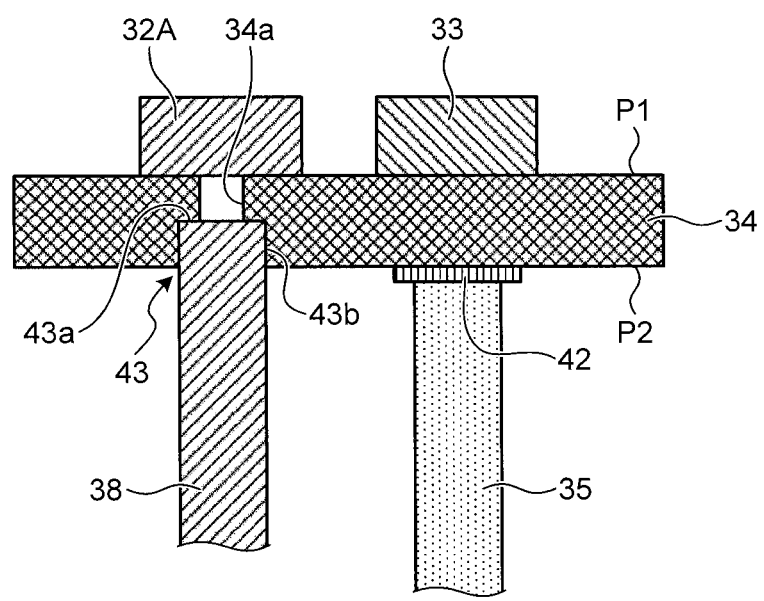
FIG. 4 is a cross sectional view of the optical transmission module along a line A-A shown in FIG. 3.

Next, the optical transmission module 100 according to the first embodiment will be explained in detail with reference to the drawings. FIG. 3 is a perspective view of the optical transmission module 100 according to the first embodiment. FIG. 4 is a cross sectional view of the optical transmission module 100 along a line A-A shown in FIG. 3.

As shown in FIG. 3, an external connection electrode 41 is provided on a main surface P1 of the circuit substrate 34 on which the optical element 32A and the electric element 33 are mounted. The external connection electrode 41 is connected to the imaging element 30 and the like via a spacer 31 that functions as an electrode and a wiring not shown. Though it is preferable that the spacer 31 has a function as an electrode, the imaging element 30 and the optical transmission module 100 may be connected by a flexible substrate. As shown in FIG. 4, a cable connection electrode 42 is provided on a rear surface P2 at an opposite side of the main surface of the circuit substrate 34 on which the optical element 32A and the electric element 33 are mounted. The cable 35 is connected to the circuit substrate 34 by using an anisotropic conductive adhesive film (ACF) and the like via the cable connection electrode 42. While the connection to the cable connection electrode 41 is made on an end surface of the cable 35 in the first embodiment, the connection may be made on a side surface of the cable 35 by exfoliating an outer insulation body and the like of the cable 35.

A hole part 34a that guides an optical beam emitted from the optical element 32A to the optical fiber 38 is provided in the circuit substrate 34 under a position where the optical element 32A is mounted. The hole part 34a is formed by hollowing out the circuit substrate 34 in a cylindrical shape along a thickness direction. On the rear surface P2 of the circuit substrate 34 at a position where the optical element 32A is mounted, an aligning and connecting part 43 that allows the optical beam emitted from the optical element 32A to be efficiently incident on the optical fiber 38 is provided. The aligning and connecting part 43 includes an abutting part 43a that allows determining a distance between the end surface of the optical fiber 38 and the optical element 32A and a guiding part 43b that allows matching an optical axis of the optical element 32A and an optical axis of the optical fiber 38. The aligning and connecting part 43 has a cylindrical shape and the guiding part 43b and the hole part 34a have the same center. A diameter of the guiding part 43b is substantially the same as that of the optical fiber 38. Besides, the abutting part 43a is formed at a position that enables a light emission surface of the optical element 32A and the end surface of the optical fiber 38 to have a predetermined distance.

It becomes possible in the optical transmission module 100 according to the first embodiment to realize a downsizing and an easy embedment in an endoscope since the alignment can be performed easily without embedding the optical element 32A and the optical fiber 38 in a case.

Figure 5:
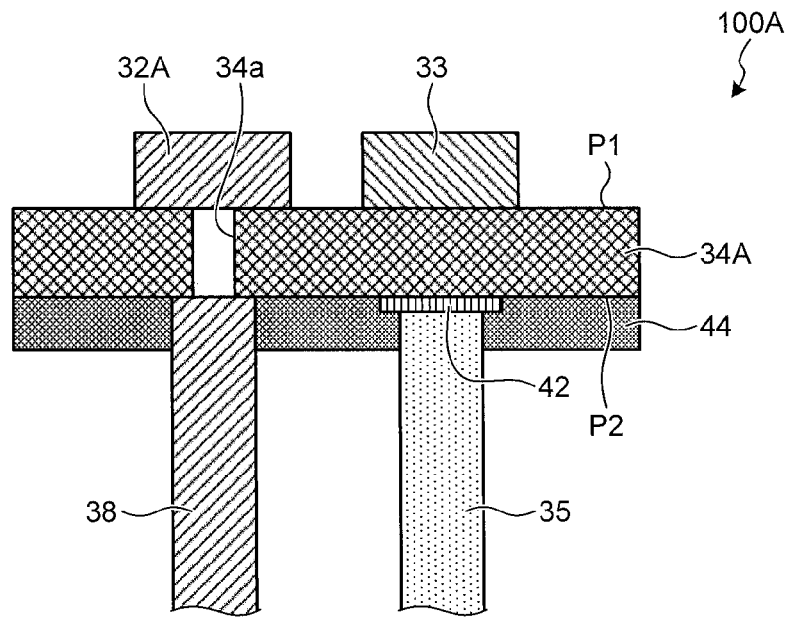
FIG. 5 is a cross sectional view of an optical transmission module according to a first modification of the first embodiment.

As a first modification of the first embodiment, an optical transmission module in which the end surface of the optical fiber 38 is connected to the circuit substrate 34 without providing the aligning and connecting part 43 on the rear surface P2 of the circuit substrate 34 can be exemplified. FIG. 5 is a cross sectional view of an optical transmission module 100A according to a first modification of the first embodiment. The optical transmission module 100A is not provided with the aligning and connecting part 43 on the rear surface P2 of a circuit substrate 34A. Besides, the optical transmission module 100A is provided with the hole part 34a that guides, in a manner of penetrating to the rear surface P2 of the circuit substrate 34A, the optical beam emitted from the optical element 32A to the optical fiber 38. In the first modification, the optical fiber 38 is sealed and fixed together with the cable 35 connecting the optical fiber 38 to the cable connection electrode 42 on the rear surface of the circuit substrate 34A by a sealing resin 44 after the end surface of the optical fiber 38 is made in direct contact with an open end face of the hole part 34a penetrating to the rear surface P2 of the circuit substrate 34A and aligned with the optical element 32A by an active alignment technique and the like. Similarly to the optical transmission module according to the first embodiment, it becomes possible also in the optical transmission module 100A according to the first modification to realize a downsizing and an embedment to an endoscope.

Second Embodiment

An optical transmission module according to a second embodiment of the present invention is different from the optical transmission module according to the first embodiment in that a circuit substrate constituting an photoelectric conversion connector includes a mounting substrate on which an optical element and an electric element are mounted and a connecting substrate to which a cable and an optical fiber are connected. The optical transmission module according to the second embodiment of the present invention will be explained below with reference to the drawings.

Figure 6:
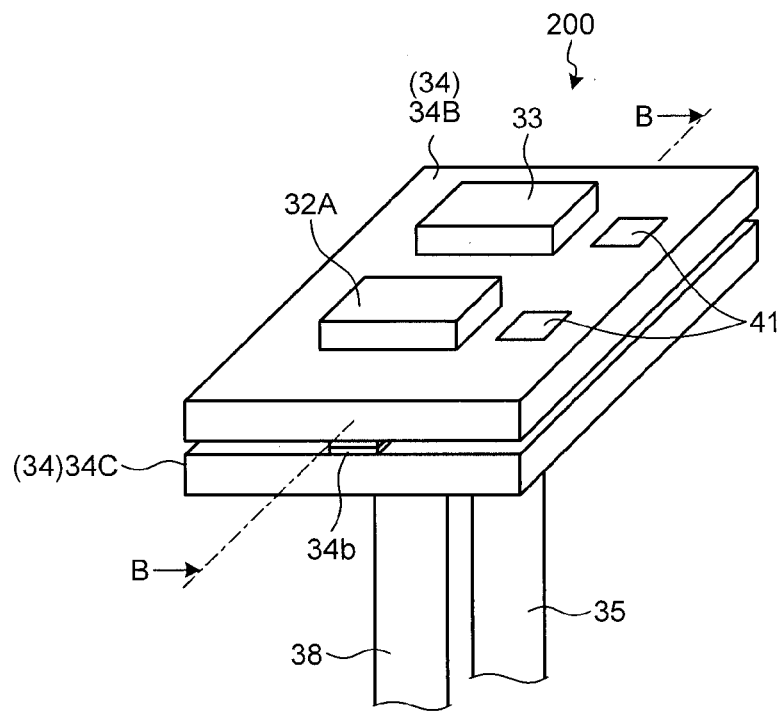
FIG. 6 is a perspective view of an optical transmission module according to a second embodiment.
Figure 7:
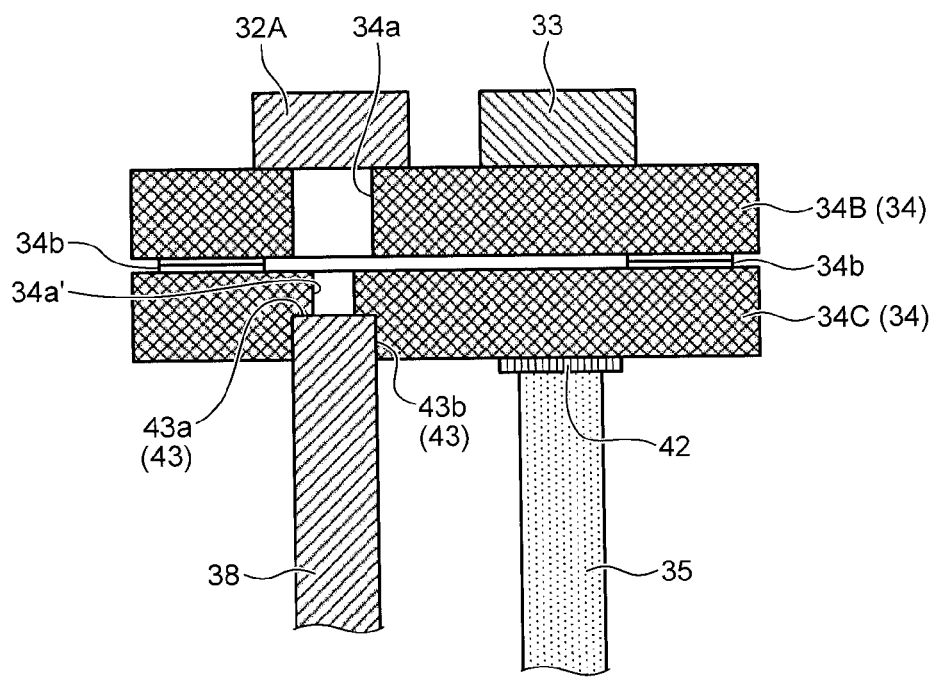
FIG. 7 is a cross sectional view of the optical transmission module along a line B-B shown in FIG. 6.

FIG. 6 is a perspective view of an optical transmission module 200 according to the second embodiment. FIG. 7 is a cross sectional view of the optical transmission module 200 along a line B-B shown in FIG. 6. As shown in FIGS. 6 and 7, a circuit substrate 34 of the optical transmission module 200 is provided with a mounting substrate 34B on which the optical element 32A and the electric element 33 are mounted and a connecting substrate 34C to which the cable 35 and the optical fiber 38 are connected.

The hole part 34a that has a cylindrical shape and guides the optical beam emitted from the optical element 32A to the optical fiber 38 is provided in the mounting substrate 34B under a position where the optical element 32A is mounted. The mounting substrate 34B and the connecting substrate 34C are connected via a spacer 34b. The cable 35 and the optical fiber 38 are connected to a rear surface side of a connection surface of the connecting substrate 34C with the mounting substrate 34B. In the connecting substrate 34C, a hole part 34a' that guides the optical beam emitted from the optical element 32A and radiated via the hole part 34a to the optical fiber 38 and the aligning and connecting part 43 that enables the optical beam emitted from the optical element 32A to be effectively radiated to the optical fiber 38 are provided. The aligning and connecting part 43 is provided with the abutting part 43a that allows determining a distance between the end surface of the optical fiber 38 and the optical element 32A and the guiding part 43b that allows an optical axis of the optical element and an optical axis of the optical fiber 38 to match. The aligning and connecting part 43 has a cylindrical shape and the guiding part 43b, the hole part 34a, and the hole part 34a' have the same center. A diameter of the guiding part 43b is substantially the same as that of the optical fiber 38. Besides, the abutting part 43a is formed at a position that enables the light emission surface of the optical element 32A and the end surface of the optical fiber 38 to have a predetermined distance.

It becomes possible in the optical transmission module 200 according to the second embodiment to realize a downsizing and an easy embedment in an endoscope since the alignment can be performed easily without embedding the optical element 32A and the optical fiber 38 in a case, similarly to the optical transmission module according to the first embodiment.

Besides, it is possible in the optical transmission module 200 according to the second embodiment to realize manufacturing in an easier manner than the manner of individually mounting the optical element 32A, the electric element 33, the cable 35, and the optical fiber 38 on one substrate since the optical transmission module is formed by separately performing the mounting of the optical element 32A and the electric element 33 onto the mounting substrate 34B and the connection of the cable 35 and the optical fiber 38 to the connecting substrate 34C and finally connecting the mounting substrate 34B and the connecting substrate 34C via the spacer 34b and the like.

While the optical transmission module 200 configured by the mounting substrate 34B and the connecting substrate 34C is explained in the second embodiment, it is possible in an optical transmission module configured such that the optical element 32A and the electric element 33 are mounted on respective mounting substrates and three or more circuit substrates are used, by arbitrarily arranging wiring for elements, providing the hole part that allows the optical beam emitted from the optical element 32A to the optical fiber 38 on each substrate, and aligning the optical element 32A and the optical fiber 38 by the aligning and connecting part 43, to obtain the same advantages. In the case of using a plurality of substrates, there is an advantage that a lot of elements can be arranged and a size (width) and a length of the optical transmission module can be arbitrarily adjusted.

Figure 8:
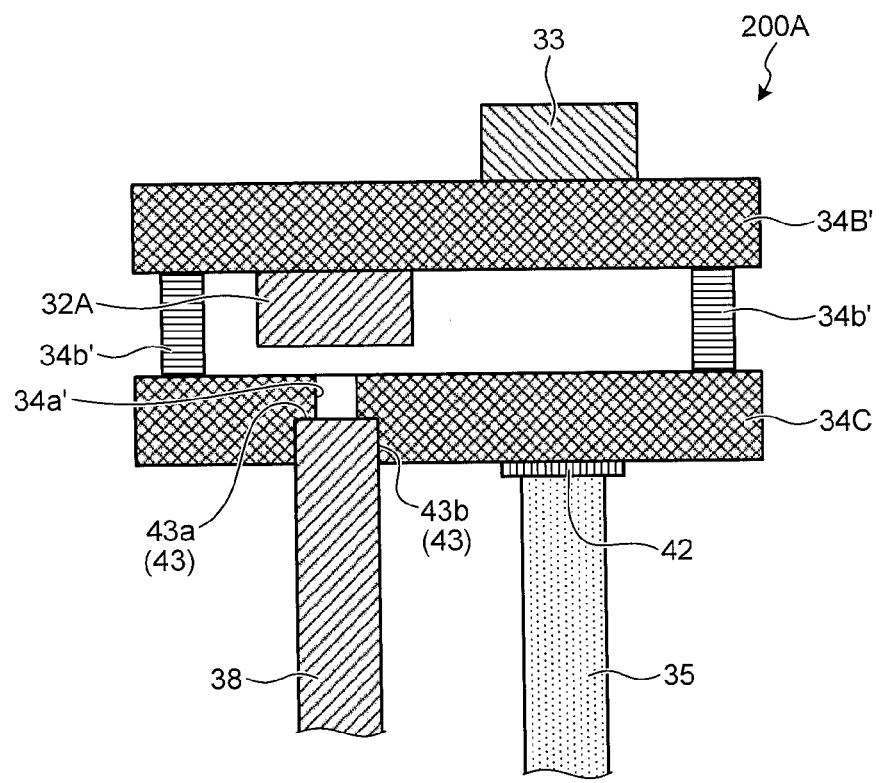
FIG. 8 is a cross sectional view of an optical transmission module according to a first modification of the second embodiment.

As a first modification of the second embodiment, an optical transmission module 200A in which an optical element is mounted on a surface, facing a connecting substrate, of a mounting substrate can be exemplified. FIG. 8 is a cross sectional view of the optical transmission module 200A according to the first modification of the second embodiment. In the optical transmission module 200A, the optical element 32A is mounted on a surface which is at a rear surface side of the surface on which the electric element 33 is mounted of a mounting substrate 34B' and faces the connecting substrate 34C. Since the optical element 32A is mounted on the surface facing the connecting substrate 34C and a light emission surface of the optical element 32A is at the side of the connecting substrate 34C, a hole part that allows guiding the optical beam emitted from the optical element is not formed in the mounting substrate 34B'. In contrast, the connecting substrate 34C to which the cable 35 and the optical fiber 38 are connected has the same configuration as the optical transmission module 200 according to the second embodiment. The mounting substrate 34B' and the connecting substrate 34C are connected via a spacer 34b' having a length not less than a height of the optical element 32A. In the optical transmission module 200A according to the first modification, the light beam emitted from the optical element 32A is radiated to the optical fiber 38 via the hole part 34a' of the connecting substrate 34C.

Third Embodiment

An optical transmission module according to a third embodiment of the present invention is different from the optical transmission module according to the second embodiment in that a condenser lens that condenses an optical beam output from an optical element or an optical beam input to the optical element and condenses an optical beam output from an optical fiber or an optical beam input to the optical fiber is provided on any one of a mounting substrate on which the optical element is mounted and a connecting substrate to which the optical fiber is connected. The optical transmission module in which the condenser lens is provided on the connecting substrate according to the third embodiment of the present invention will be explained below with reference to the drawings. While the condenser lens is provided in the connecting substrate in the third embodiment, the condenser lens may condense the optical beam on a light receiving surface of a light receiving element, may be provided in the mounting substrate as long as the optical beam can be condensed in the core on the end surface of the optical fiber, or respective condenser lenses may be arranged in the mounting substrate and the connecting substrate.

Figure 9:
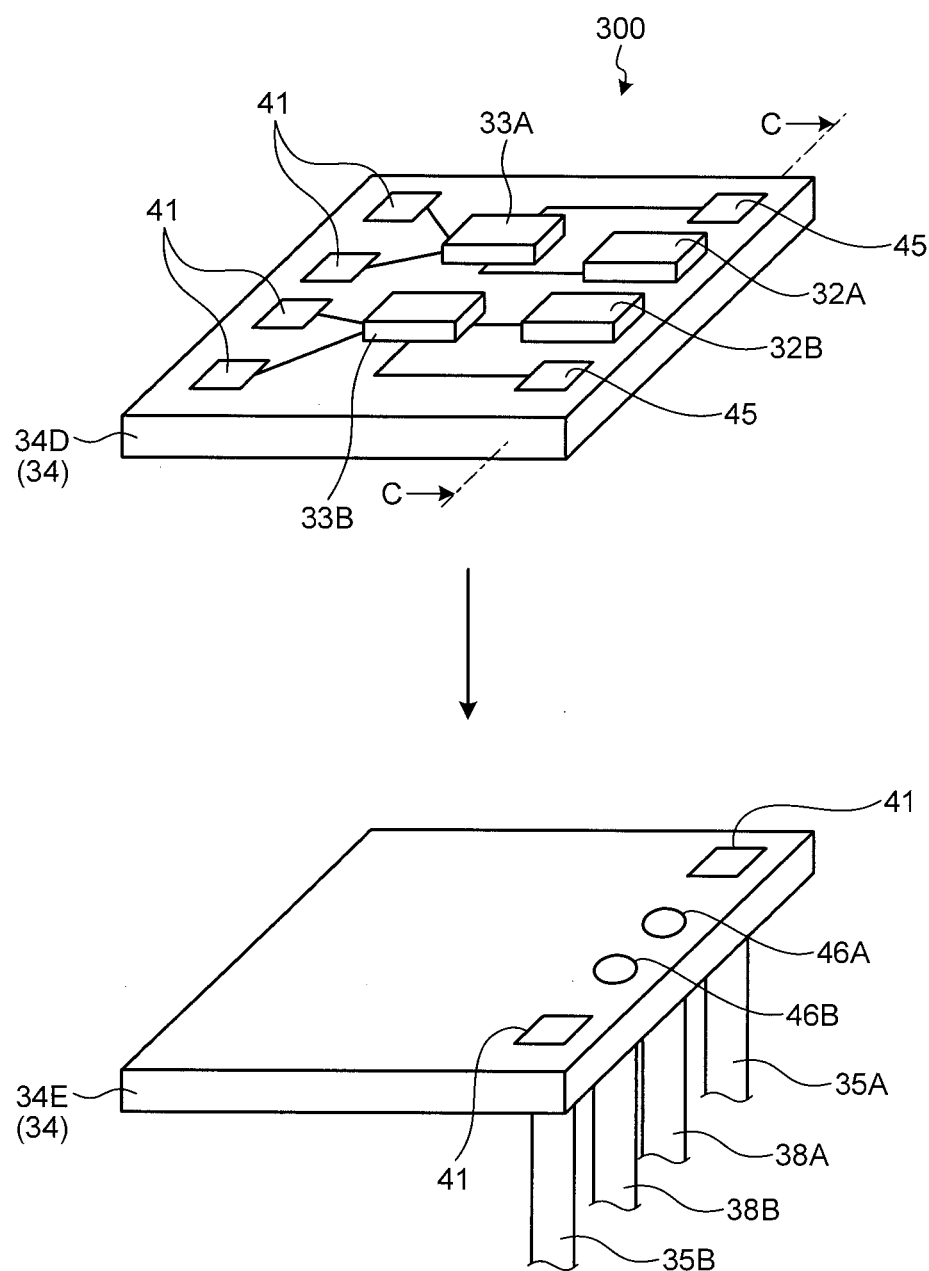
FIG. 9 is a perspective view in which a mounting substrate and a connecting substrate which constitute an optical transmission module according to a third embodiment are disintegrated and displayed.
Figure 10:
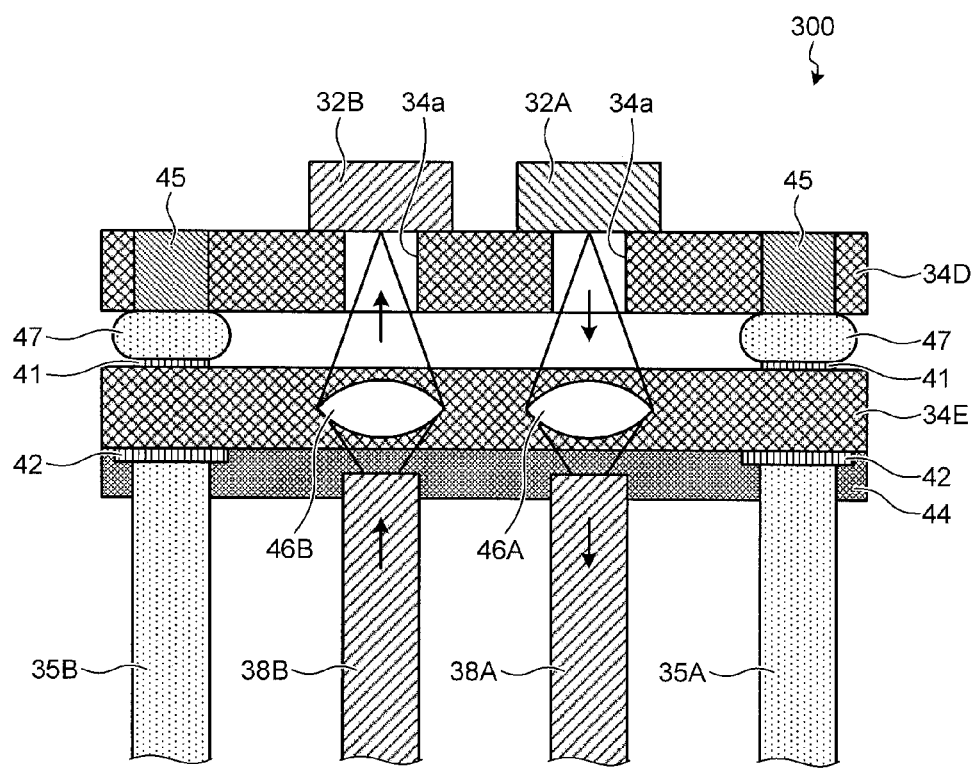
FIG. 10 is a cross sectional view along a line C-C in a state where the optical transmission module shown in FIG. 9 is assembled.

FIG. 9 is a perspective view in which a mounting substrate and a connecting substrate which constitute an optical transmission module 300 according to the third embodiment are disintegrated and displayed. FIG. 10 is a cross sectional view along a line C-C in a state where the optical transmission module shown in FIG. 9 is assembled. As shown in FIGS. 9 and 10, a circuit substrate 34 of the optical transmission module 300 includes a mounting substrate 34D on which the optical element 32A, a light receiving element 32B, electric elements 33A and 33B, the external connection electrode 41, and a penetration electrode 45 are mounted and a connecting substrate 34E to which cables 35A and 35B and optical fibers 38A and 38B are connected.

The light receiving element 32B receives optical signals such as clock signals transmitted from the signal processing device via the optical fiber 38B. The electric element 33A controls an electric/optical signal conversion of electric signals input to the optical element 32A and also controls light emission of optical signals to be transmitted. The electric element 33B controls a light reception of optical signals input to the light receiving element 32B and also controls an optical/electric signal conversion. Besides, the mounting substrate 34D and the connecting substrate 34E are connected by a solder ball 47 and the electric elements 33A and 33B are connected to the cables 35A and 35B respectively by the penetration electrode 45. An amount of the solder ball 47 to be used for the connection between the mounting substrate 34D and the connecting substrate 34E is determined by taking a distance between focal points of condenser lenses 46A and 46B into consideration. Here, the solder ball 47 shown is no longer a ball state since the figure shows a state after the connection, however, solder ball is used as a name for the reference number 47 in embodiments for the sake of convenience.

In the connecting substrate 34E, the condenser lenses 46A and 46B are arranged. It is preferable that the connecting substrate 34E is a glass substrate and the condenser lenses 46A and 46B are formed of an optically-transparent material such as a thermosetting resin integrally with the connecting substrate 34E. Or, fitting parts for the condenser lenses 46A and 46B may be formed in a substrate formed of a metal material and the condenser lenses 46A and 46B may be arranged therein.

Under the control of the electric element 33A, the optical beam emitted from the optical element 32A is radiated to the condenser lens 46A via the hole part 34a and the optical beam radiated to the condenser lens 46A is condensed in the core on the end part of the optical fiber 38A from the condenser lens 46A. The optical beam emitted from the optical fiber 38B is radiated to the condenser lens 46B and the optical beam radiated to the condenser lens 46B is condensed by the condenser lens 46B on a light receiving surface of the light receiving element 32B via the hole part 34a. After aligning the condenser lens 46A and the optical fiber 38A, and the condenser lens 46B and the optical fiber 38B, the optical fibers 38A and 38B are sealed and fixed by the sealing resin 44 together with the cables 35A and 35B. The sealing resin 44 is selected among optically-transparent materials.

It becomes possible in the optical transmission module 300 according to the third embodiment to realize a downsizing and an easy embedment in an endoscope since the distance between the optical element and the optical fiber can be adjusted while keeping an amount of optical beams to be transmitted by using the condenser lenses 46A and 46B, and the optical element 32A, the light receiving element 32B, and the optical fibers 38A and 38B are aligned without being embedded in a case and arranged in the direction of the thickness of the mounting substrate 34D and the connecting substrate 34E. This configuration in arrangement enables suppressing a growth in size along a longitudinal direction of the optical fiber and the like even in a multifunctional optical transmission module having an increased number of elements to be mounted.

Moreover, it is possible in the optical transmission module 300 according to the third embodiment to realize manufacturing in an easier manner than the manner of individually mounting elements and cables on one substrate since the optical transmission module is formed by separately performing the mounting of the elements including the optical element 32A onto the mounting substrate 34D and the connection of the cable 35A and the like to the connecting substrate 34E and finally connecting the mounting substrate 34D and the connecting substrate 34E via the solder ball 47 and the like. In addition, since the mounting substrate 34D and the connecting substrate 34E are connected by using a predetermined amount of solder ball, it is possible to align the optical element 32A and the optical fiber 38A, and the light receiving element 32B and the optical fiber 38B easily thanks to a self-aligning function and a height-adjusting function of the solder ball.

Figure 11:
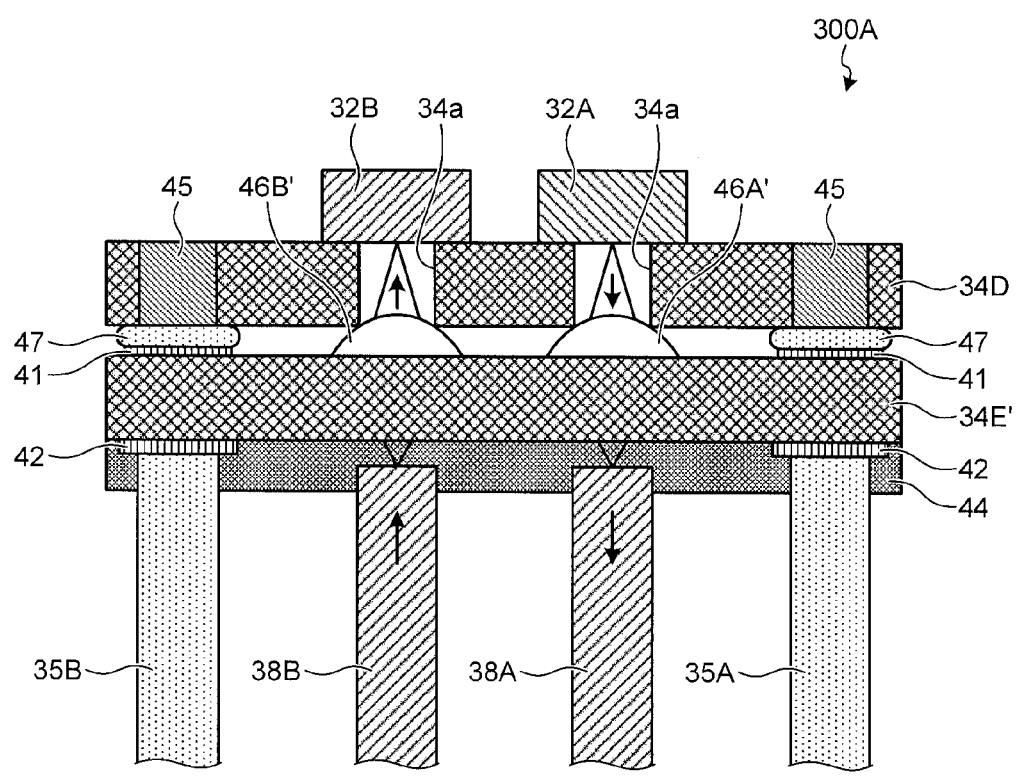
FIG. 11 is a cross sectional view of an optical transmission module according to a first modification of the third embodiment.

As a first modification of the third embodiment, an optical transmission module 300A in which a condenser lens is provided in a protruding manner on a connection substrate can be exemplified. FIG. 11 is a cross sectional view of an optical transmission module 300A according to the first modification of the third embodiment. The optical transmission module 300A is provided with condenser lenses 46A' and 46B' in a protruding manner on a connecting substrate 34E' which is a glass substrate. After aligning the condenser lens 46A' and the optical fiber 38A, and the condenser lens 46B' and the optical fiber 38B similarly to the third embodiment, the optical fibers 38A and 38B are sealed and fixed by the sealing resin 44 together with the cables 35A and 35B. The sealing resin 44 is selected among optically-transparent materials.

The optical element 32A and the light receiving element 32B are aligned and mounted with respect to the hole parts 34a provided for transmission of light on the mounting substrate 34D. The condenser lenses 46A' and 46B' provided in the protruding manner on the connecting substrate 34E' are made in direct contact with the hole parts 34a of the mounting substrate 34D, the optical element 32A and the optical fiber 38A, and the light receiving element 32B and the optical fiber 38B are aligned, and the mounting substrate 34D and the connecting substrate 34E' are connected by the solder ball 47. The direct contact between curved surfaces of the condenser lenses 46A' and 46B' and the hole parts 34a causes a centering action, so that the optical element 32A and the optical fiber 38A, and the light receiving element 32B and the optical fiber 38B can be aligned easily.

Fourth Embodiment

An optical transmission module according to a fourth embodiment of the present invention is different from the optical transmission module according to the third embodiment in that the arrangement of cables and optical fibers is made such that the cables or the optical fibers do not neighbor in connecting a plurality of cables and optical fibers that perform a signal transmission with the signal processing device as an external device to the connecting substrate. The optical transmission module according to the fourth embodiment of the present invention will be explained below with reference to the drawings. While a case of arranging five cables and five optical fibers at regular intervals vertically in two lines and horizontally in five lines is taken as an example in the explanation in the third embodiment, it is only necessary to arrange a cable (or an optical fiber) at a position most adjacent to a cable (or an optical fiber) of different kind arranged at a particular position and the present invention is not limited to this example.

Figure 12:
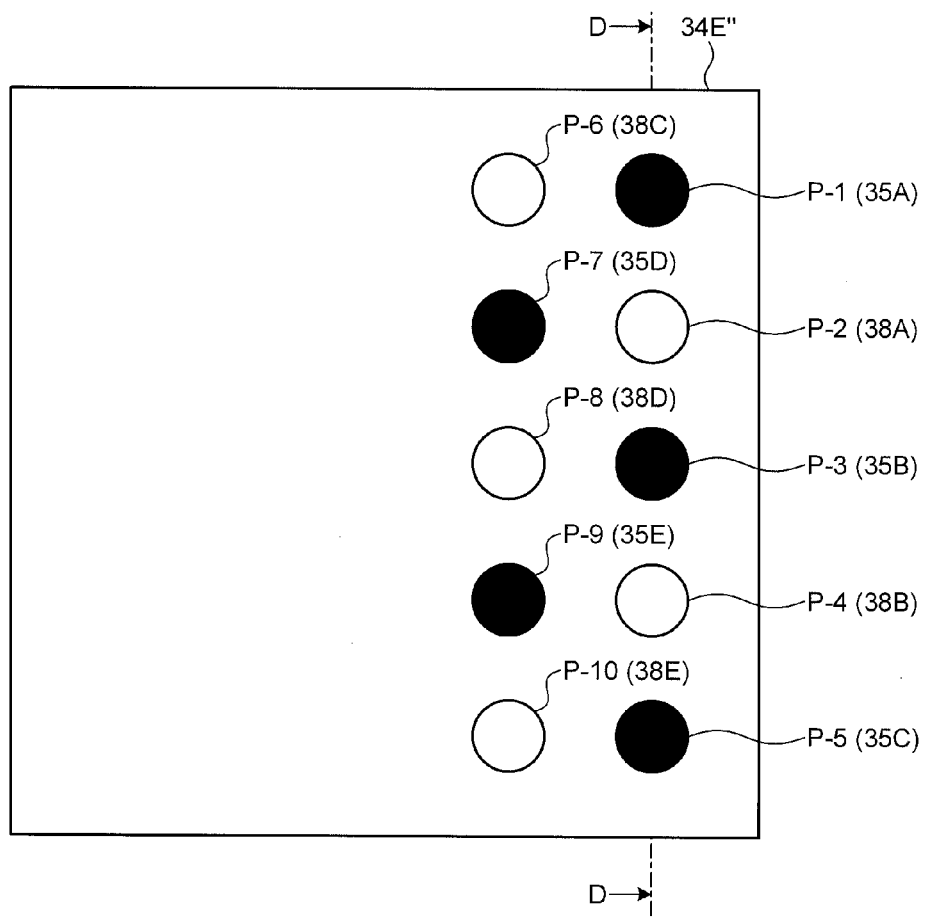
FIG. 12 is a plane view of an array of cables and optical fibers in an optical transmission module according to a fourth embodiment.
Figure 13:
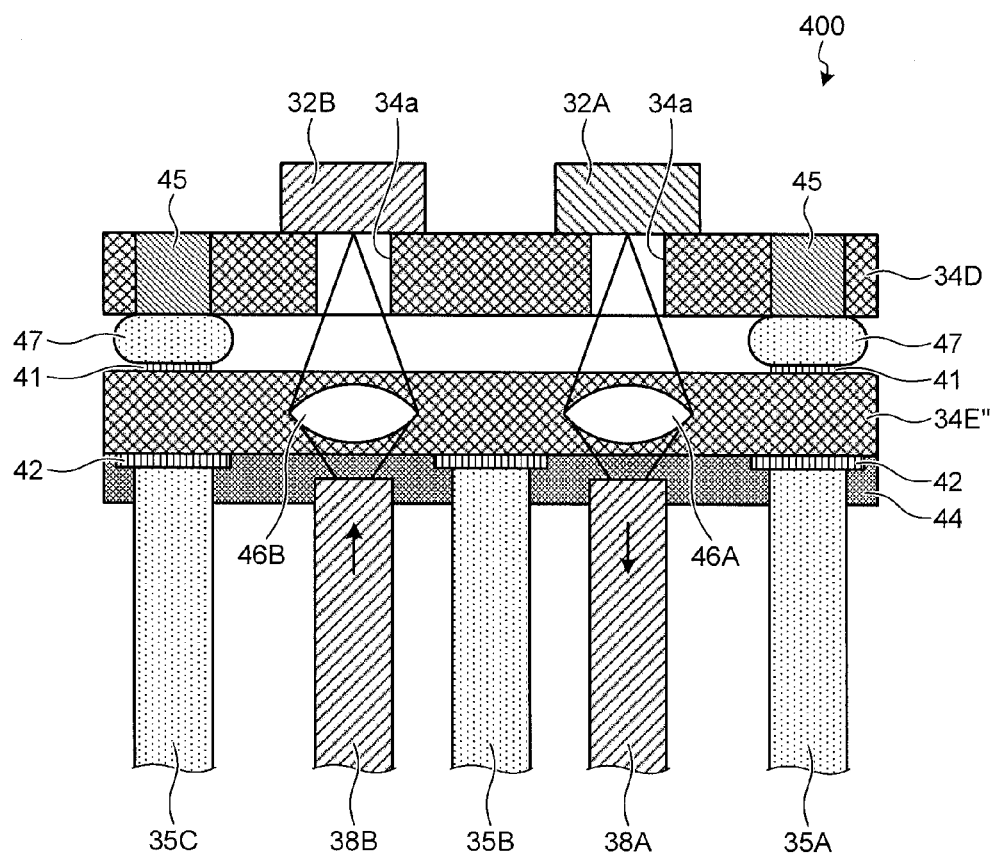
FIG. 13 is a cross sectional view of the optical transmission module according to the fourth embodiment at a position along a line D-D shown in FIG. 12.

FIG. 12 is a plane view of an array of cables 35 and optical fibers 38 in an optical transmission module 400 according to the fourth embodiment. FIG. 13 is a cross sectional view of the optical transmission module 400 according to the fourth embodiment at a position along a line D-D shown in FIG. 12. As shown in FIG. 13, the cables 35A, 35B, and 35C and the optical fibers 38A and 38B are connected to a connecting substrate 34E", and the cable 35 and the optical fiber 38 are arranged alternately in such an order as the cable 35A, the optical fiber 38A, the cable 35B, the optical fiber 38B, and the cable 35C. Besides, the optical transmission module 400 is provided with cables 35D and 35E and optical fibers 38C, 38D, and 38E, which are not shown in FIG. 13, in parallel with the cables 35A, 35B, and 35C and the optical fibers 38A and 38B.

The cable 35A, the optical fiber 38A, the cable 35B, the optical fiber 38B, and the cable 35C are respectively connected and arranged at positions P-1, P-2, P-3, P-4, and P-5 shown in FIG. 12. The optical fiber 38C, the cable 35D, the optical fiber 38D, the cable 35E, and the optical fiber 38E are respectively connected and arranged at positions P-6, P-7, P-8, P-9, and P-10 shown in FIG. 12. The cable 35 and the optical fiber 38, which are different kinds from each other, are arranged so that one kind is adjacent to the other, for example, the cables 35B, 35D, and 35E are arranged respectively at the positions P-3, P-7, and P-9 which are most adjacent to the optical fiber 38D arranged at the position P-8. This arrangement enables preventing an occurrence of crosstalk due to electric signals and optical signals transmitted by the cables 35 and the optical fibers 38.

While the embodiments of the present invention are explained so far, the present invention may cover various embodiments not explained herein, and various modifications may be made without departing from the technical ideas as defined by the appended claims.

According to the present invention, it becomes possible in the photoelectric conversion connector provided with an electric element, an optical element, at least one substrate on which a cable and an optical fiber are mounted to reduce, without using a case, the size of the photoelectric conversion connector by having a configuration such that the cable and the optical fiber are mounted on the same surface of the substrate, the electric element and the optical element are mounted and arranged on a surface, different from the surface on which the cable and the optical fiber are mounted, of the substrate, and the electric element and the cable in line, and the optical element and the optical fiber in line are mounted and arranged in the direction of the thickness of the substrate.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A photoelectric conversion connector, comprising:
   an optical element configured to convert an electric signal to an optical signal;
   an electric element configured to control the optical element to vary at least one of a light emission and a light reception of the optical signal;
   an optical fiber configured to transmit the optical signal, as varied by the electric element, to an external device;
   a substrate having a first surface on which the electric element and the optical element are mounted and a second surface, opposite to the first surface, on which the optical fiber is mounted,
   wherein the substrate comprising an aligning and connecting part configured to optically connect the optical fiber to the optical element; and
   the optical fiber being mounted to the substrate along a direction orthogonal to the first and second surfaces of the substrate.

2. The photoelectric conversion connector according to claim 1, further comprising a cable that performs at least one of inputting and outputting the electric signal to the electric element connected to the second surface, and an external connection electrode is provided on the first surface.

3. The photoelectric conversion connector according to claim 2, further comprising a cable connection electrode that connects the cable is provided on the second surface.

4. The photoelectric conversion connector according to claim 2, further comprising a circuit that performs a signal conversion relaying process between the optical element and the electric element is formed on the substrate, the circuit supplying an electric power to the substrate, transmitting and receiving the electric signal via the cable, and transmitting and receiving the optical signal to the optical element via the optical fiber.

5. The photoelectric conversion connector according to claim 2, wherein, in a case of connecting a plurality of cables and optical fibers to the substrate, a connection arrangement of the cables and the optical fibers to the substrate is made by arranging the cable and the optical fiber, which are different in kind from each other, so that one kind is adjacent to the other kind.

6. An imaging apparatus, wherein the external device is an imaging element connected to the external connection electrode of the photoelectric conversion connector according to claim 2.

7. The imaging apparatus according to claim 6, wherein a main surface of the imaging element is arranged in parallel with the substrate for the photoelectric conversion connector.

8. The imaging apparatus according to claim 6, further comprising an electrode formed on a rear surface of the imaging element and the external connection electrode are connected.

9. The imaging apparatus according to claim 6, wherein the imaging element and the substrate are connected via a flexible substrate.

10. An endoscope comprising the imaging apparatus according to claim 6.

11. The photoelectric conversion connector according to claim 1, wherein
   the substrate includes a mounting substrate having the first surface on which at least the optical element and the electric element are mounted and a connecting substrate having the second surface to which a cable that performs at least one of inputting and outputting the electric signal to the electric element is connected, and
   the mounting substrate and the connecting substrate are connected via a spacer that allows an adjustment so that a diameter of one of an optical beam emitted by the optical element and an optical beam received by the optical element nearly corresponds to a diameter of a core of the optical fiber, and an external connection electrode is provided on the first surface of the mounting substrate.

12. The photoelectric conversion connector according to claim 11, wherein the spacer is an electrode that connects the mounting substrate and the connecting substrate.

13. The photoelectric conversion connector according to claim 11, wherein the spacer is a solder ball.

14. The photoelectric conversion connector according to claim 11, wherein at least one of the mounting substrate and the connecting substrate includes a condenser lens that condenses one of an optical beam emitted by the optical element and an optical beam received by the optical element.

15. The photoelectric conversion connector according to claim 14, wherein the condenser lens is formed integrally with at least one of the mounting substrate and the connecting substrate which are formed of an optically-transparent material.

16. The photoelectric conversion connector according to claim 15, wherein the condenser lens is provided in a manner of protruding on the connecting substrate; and
   the optical element and the optical fiber are aligned by making a protruding curved lens surface of the condenser lens in direct contact with a hole part formed on the mounting substrate.

17. The photoelectric conversion connector according to claim 1, wherein the aligning and connecting part includes an abutting part that allows determining a distance between an end surface of the optical fiber and the optical element, and a guiding part that allows matching an optical axis of the optical element and an optical axis of the optical fiber.

18. The photoelectric conversion connector according to claim 1, wherein the optical fiber includes an end mounted to the substrate and the end is mounted to the substrate at a position between the first and second surfaces.

19. An optical transmission device, comprising:
   an optical element configured to convert an electric signal to an optical signal;
   an electric element configured to control the optical element to vary at least one of a light emission and a light reception of the optical signal;
   a cable that performs at least one of inputting and outputting the electric signal to the electric element;
   an optical fiber configured to transmit the optical signal, as varied by the electric element, to an external device; and
   a substrate having a first surface on which the electric element and the optical element are mounted and a second surface, opposite to the first surface, on which the optical fiber and the cable are mounted,
   wherein the optical fiber and the cable each being mounted to the substrate along a direction orthogonal to the first and second surfaces of the substrate.

20. The optical transmission device according to claim 19, wherein the optical fiber includes an end mounted to the substrate and the end is mounted to the substrate at a position between the first and second surfaces.

* * * * *